(12) United States Patent
Lualdi

(10) Patent No.: US 12,324,571 B2
(45) Date of Patent: Jun. 10, 2025

(54) AUTOMATED PUNCHING STATION FOR THE PRODUCTION OF PUNCHED COMPONENTS, PUNCHED COMPONENT AND RELATIVE PRODUCTION METHOD

(71) Applicant: HPF S.R.L., Fagagna (IT)

(72) Inventor: Gabriele Lualdi, Fagagna (IT)

(73) Assignee: HPF S.R.L., Fagagna (IT)

( * ) Notice: Subject to any disclaimer, the term of this patent is extended or adjusted under 35 U.S.C. 154(b) by 379 days.

(21) Appl. No.: 17/396,651

(22) Filed: Aug. 6, 2021

(65) Prior Publication Data

US 2022/0040877 A1 Feb. 10, 2022

(51) Int. Cl.
| | | |
|---|---|---|
| *B26F 1/40* | (2006.01) | |
| *A61B 17/00* | (2006.01) | |
| *B26D 5/08* | (2006.01) | |

(52) U.S. Cl.
CPC ............... *A61B 17/00* (2013.01); *B26D 5/08* (2013.01); *B26F 1/40* (2013.01); *A61B 2017/00526* (2013.01)

(58) Field of Classification Search
CPC ........ B21D 28/26; B21D 28/28; B21D 28/32; B21D 28/24; B21D 7/02; B26D 7/02; B26F 1/40; B26F 1/14
See application file for complete search history.

(56) References Cited

U.S. PATENT DOCUMENTS

| | | | | |
|---|---|---|---|---|
| 9,681,881 | B1 * | 6/2017 | Billiet | .................. A61L 31/026 |
| 2003/0135219 | A1 * | 7/2003 | Salyer | ............... A61B 17/1677 |
| | | | | 606/81 |
| 2005/0113837 | A1 * | 5/2005 | Salyer | ............... A61B 17/1666 |
| | | | | 606/80 |
| 2010/0269652 | A1 * | 10/2010 | Becker | ................. B26D 7/0633 |
| | | | | 83/30 |
| 2013/0245628 | A1 * | 9/2013 | Sidebotham | ....... A61B 17/1666 |
| | | | | 219/121.64 |

FOREIGN PATENT DOCUMENTS

| | | | | |
|---|---|---|---|---|
| CN | 108858451 A | | 11/2018 | |
| DE | 102009058633 A1 | * | 6/2011 | .......... B25J 15/0052 |
| DE | 102013111337 A1 | * | 4/2015 | ............ B21D 28/04 |
| DE | 102017119550 A1 | * | 2/2019 | ............ B21D 28/24 |
| WO | WO-03/059178 A1 | | 7/2003 | |
| WO | WO-2018006506 A1 | * | 1/2018 | ............ B21D 28/02 |
| WO | WO-2018145439 A1 | * | 8/2018 | ............... B26D 7/06 |

OTHER PUBLICATIONS

Search Report for IT 202000019408, dated Apr. 9, 2021.

* cited by examiner

*Primary Examiner* — Jennifer S Matthews
(74) *Attorney, Agent, or Firm* — MARSHALL, GERSTEIN & BORUN LLP

(57) ABSTRACT

The invention relates to an automated punching station for the production of punched components for prosthetic surgery instruments, in particular for instruments able to mill/cut or otherwise carry out tissue removal processes in preparation for, or in the context of, prosthetic surgery operations. The invention also concerns a method to produce said punched components, and a punched component thus obtained.

10 Claims, 4 Drawing Sheets

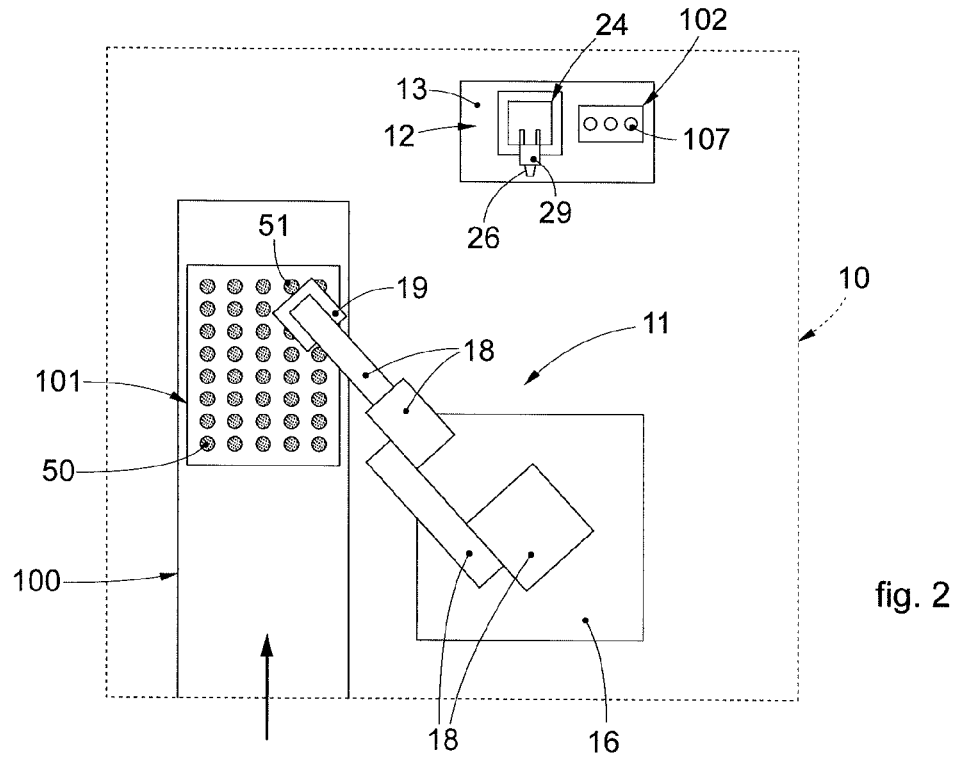
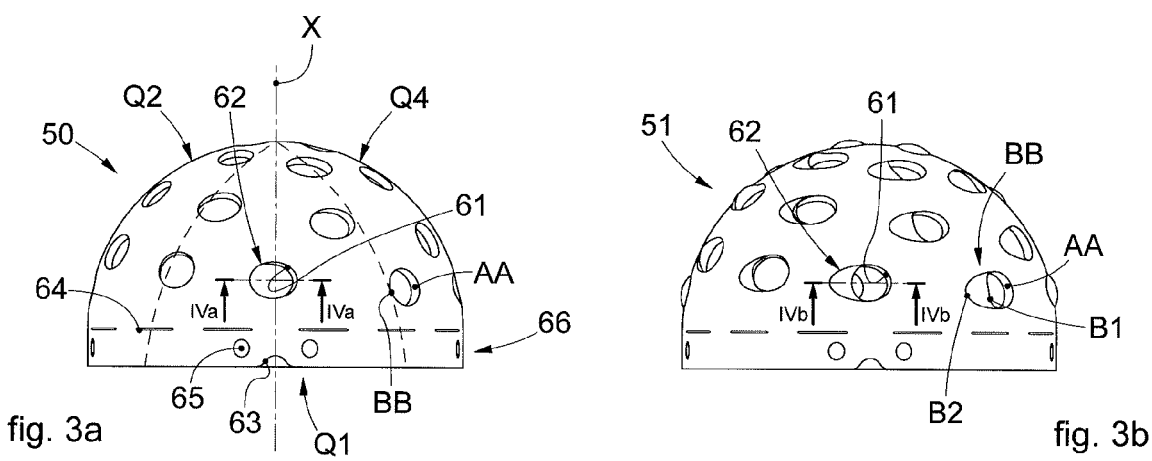
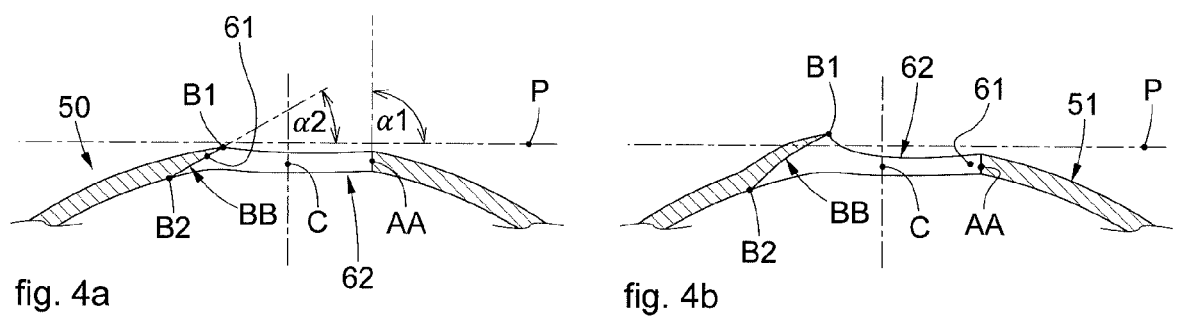
fig. 2
fig. 3a  fig. 3b
fig. 4a  fig. 4b

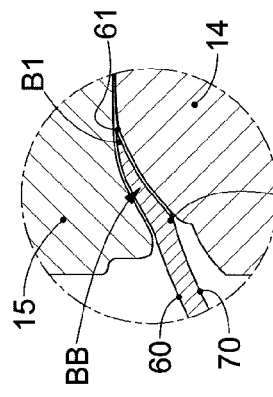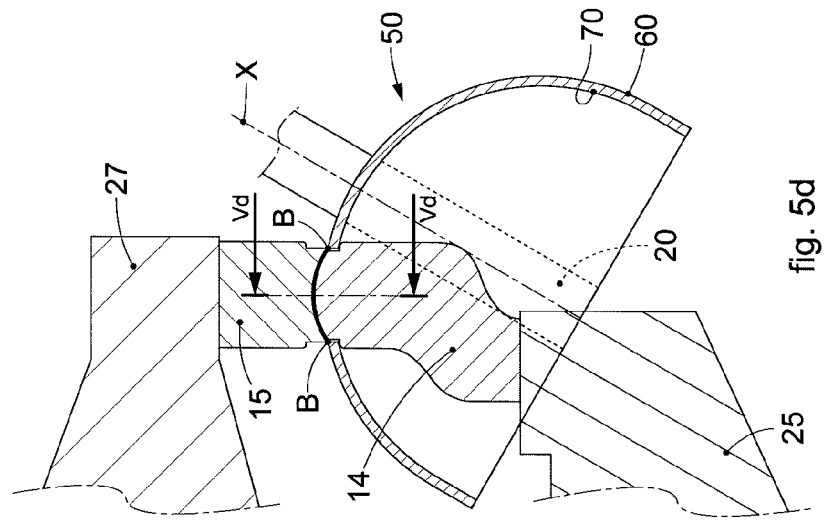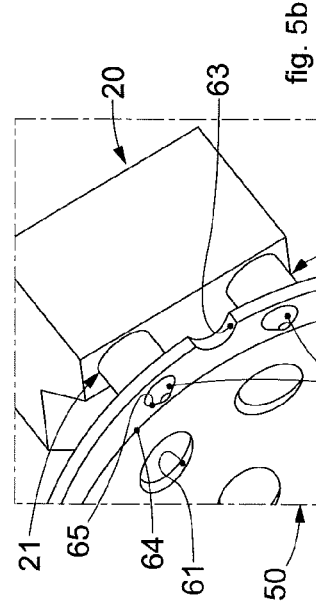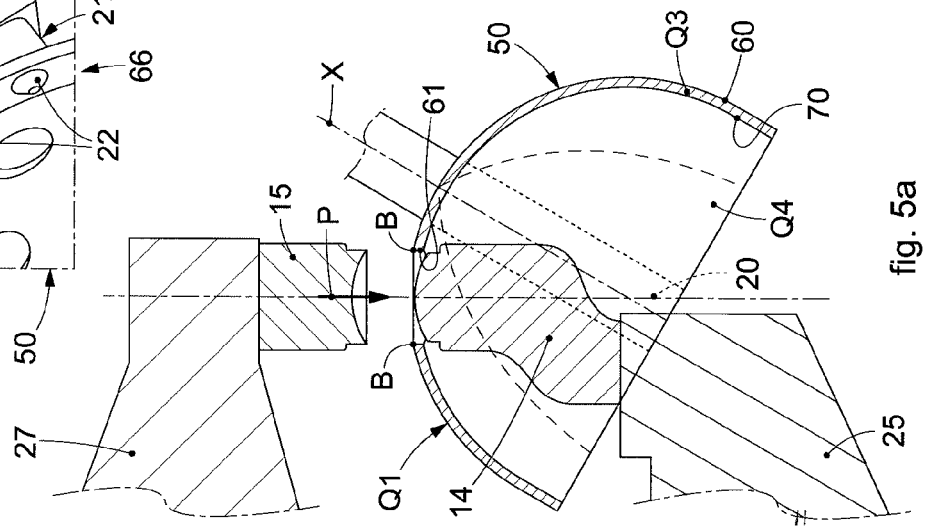

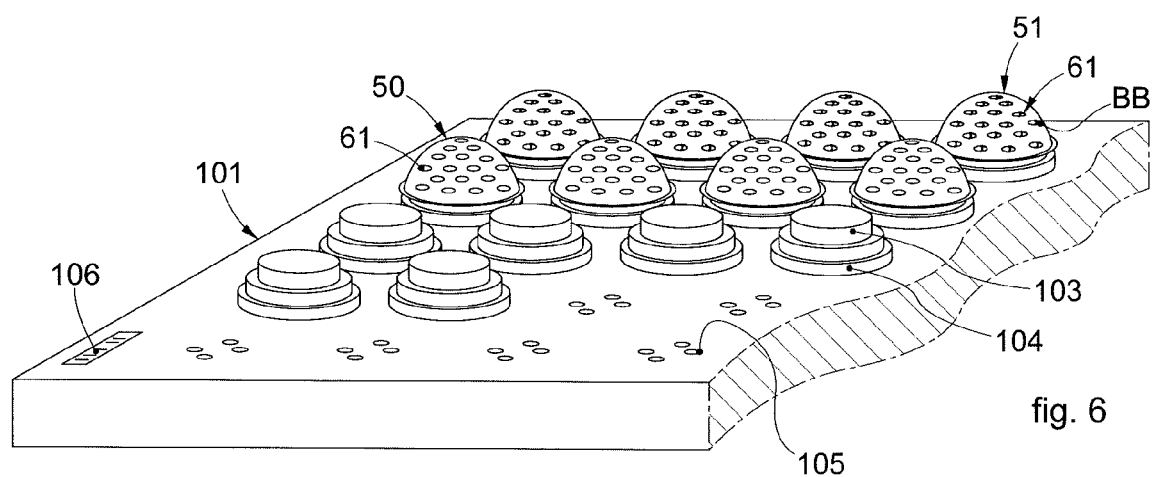
fig. 6
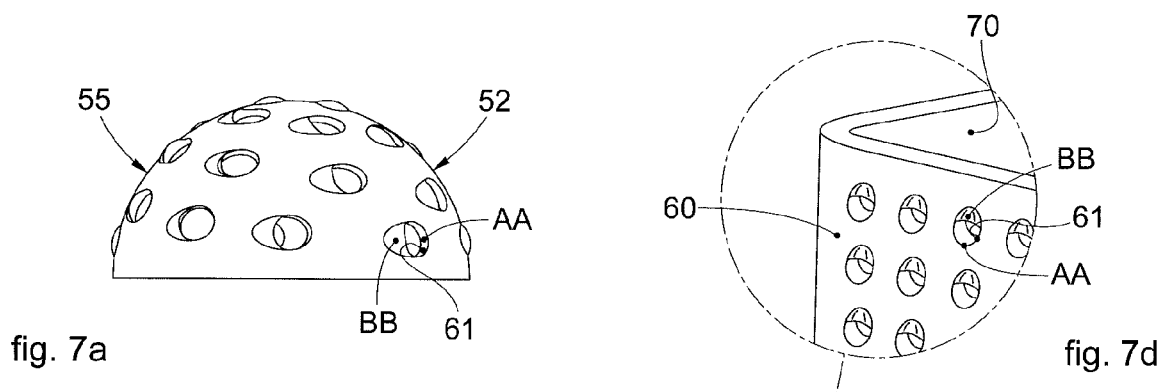
fig. 7a
fig. 7d
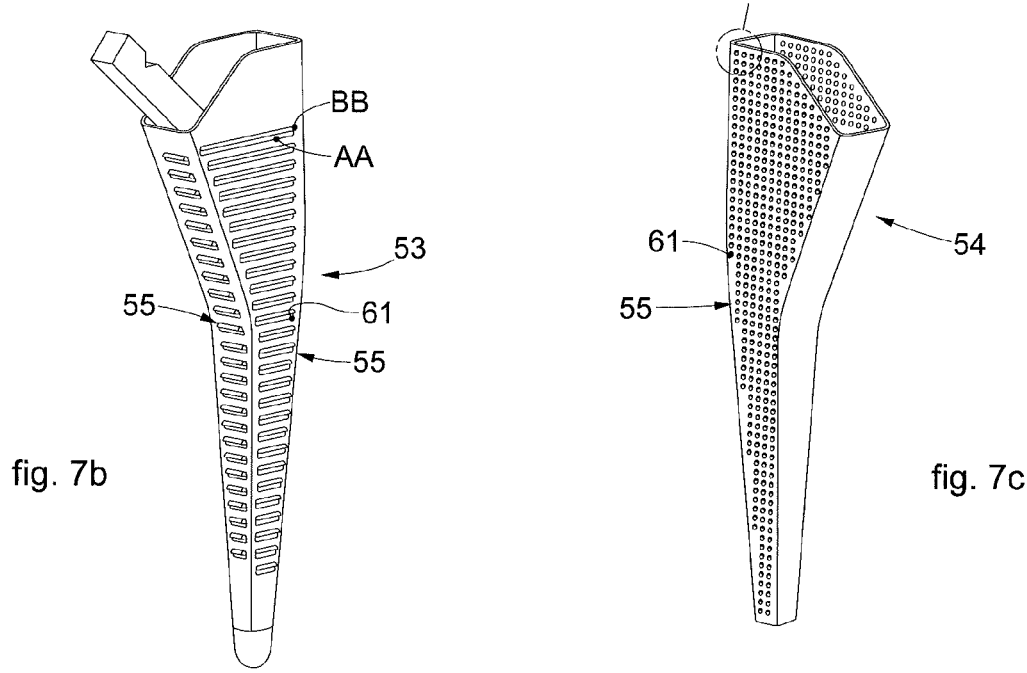
fig. 7b
fig. 7c

AUTOMATED PUNCHING STATION FOR THE PRODUCTION OF PUNCHED COMPONENTS, PUNCHED COMPONENT AND RELATIVE PRODUCTION METHOD

FIELD OF THE INVENTION

The present invention relates to an automated station for the production of punched components for prosthetic surgery instruments, in particular punched components which, once finished, are able to mill/cut or otherwise carry out tissue removal processes in preparation for, or in the context of, prosthetic surgery operations, in this case in the orthopaedic field.

The invention also concerns a method to produce such a punched component, and the punched component thus obtained.

BACKGROUND

In general, prosthetic surgery instruments are known which are able to remove bone tissues by milling, cutting, abrasion and shaped to produce coordinated and conjugated bone sites suitable for the arrangement and implantation of relative components of surgical prostheses. Such instruments may be, for example, acetabular cutters, patellar cutters, glenoid cutters, rasps, broaches or similar or comparable instruments.

The aforementioned known instruments generally include an internally hollow cutting body, having a size related to the bone site to be made. On an external surface of the cutting body, a plurality of through holes are made, which are provided with sharp and protruding edges, able to carry out a mechanical excavation on the bone.

Typically, the cutting body is produced starting from an untreated component in metal material, for example, but not only, titanium or steel, which is fed to a production facility of such instruments which comprises in sequence a chip removal machine and/or a laser cutting apparatus, a sharpening machine, a grinding machine, and a punching machine, to then undergo appropriate finishing treatments.

In particular, chip removal machines or laser cutting apparatuses are used at least for the production of the aforementioned through holes and any auxiliary apertures functional for the subsequent workings.

One drawback of current production facilities is that they require manual intervention by an operator in some of the working steps. In particular, in the punching working, an operator manipulates the component to place it in cooperation with a punching press. The need for human intervention makes it impossible to ensure a good repeatability of the working results, as well as a risk to the safety of the operator themself, who necessarily enters the range of action of the machine.

In addition, the required activity is repetitive and tiring, and the operator may need pause intervals close in time, causing a decrease in productivity.

There is therefore a need to improve an automated station for the production of punched components for prosthetic surgery instruments that can overcome at least one of the drawbacks of the prior art.

In particular, an objective of the present invention is to provide an automated punching station able to reduce, as much as possible, the need for intervention by an operator for the execution of the working.

Another objective is to increase the repeatability of the working and the productivity of the process.

A further objective is to develop a method to produce a punched component in the aforementioned automated punching station.

The Applicant has studied, tested and realised the present invention to overcome the drawbacks of the prior art, and to obtain these and further objectives and advantages.

SUMMARY

The present invention is expressed and characterised in the independent claims. The dependent claims show other features of the present invention or variants of the main solution idea.

In accordance with the aforementioned objectives, an automated punching station for the production of punched components which exceeds the limits of the prior art and eliminates the defects present therein is disclosed.

The automated punching station in accordance with the present invention may be suitable for insertion into a robotic working line for the automated production of prosthetic surgery instruments.

The punching station is able to produce the aforementioned punched components which are able, once finished, to be used in prosthetic surgery instruments. Such punched components are produced starting from hollow intermediate components which have at least one external surface and an opposite internal surface.

According to embodiments, the intermediate components have through holes having at least a segment of the edge sharp.

The aforementioned punching station comprises:
a transport support, able to receive and position a plurality of intermediate components, each provided with through holes defined by a respective edge;
a press device comprising at least one fixed punch and a counter-punch mobile in a punching direction with respect to said fixed punch for punching each of said edges for the purpose of producing a cutting part of the prosthetic surgery instrument;
at least one automated operator configured to pick up, and move one at a time, said intermediate components from said transport support, so as to place each intermediate component in cooperation on each occasion with said press device in order to punch a respective edge;
a control unit configured at least to command the automated operator to maintain each intermediate component in a grip once placed in cooperation with the press device and move said automated operator synchronously, and in the same punching direction, with respect to said counter-punch, so as to accompany said intermediate component in said punching direction when said counter-punch engages said intermediate component in the punching operation.

In accordance with the aforementioned objectives, a method to produce punched components for prosthetic surgery instruments and a punched component thus made are also disclosed.

BRIEF DESCRIPTION OF THE DRAWINGS

These and other aspects, features and advantages of the present invention will become clear from the following embodiment disclosure, given as a non-limiting example, with reference to the attached drawings in which:

FIG. 2 is a schematic top view of FIG. 1;

FIGS. 3a-b are side views of a possible intermediate component which has a spherical cap shape, and of a punched component obtained from the intermediate component according to embodiments disclosed herein;

FIGS. 4a-b are sectional views with respect to the planes IVa-IVa, IVb-IVb of details of the components of FIGS. 3a-b;

FIGS. 5a, c, d are schematic sectional views illustrating the punching operation;

FIG. 5b is a schematic perspective view of an enlarged detail of FIG. 5a;

FIG. 5e is a sectional view with respect to the plane Ve-Ve of an enlarged detail of FIG. 5d;

FIG. 6 is a three-dimensional view of intermediate and punched components positioned on a transport support according to embodiments;

FIGS. 7a-c are three-dimensional views of cutting bodies according to embodiments;

FIG. 7d is a three-dimensional view of an enlarged detail of the cutting body of FIG. 7c.

Figure 1:
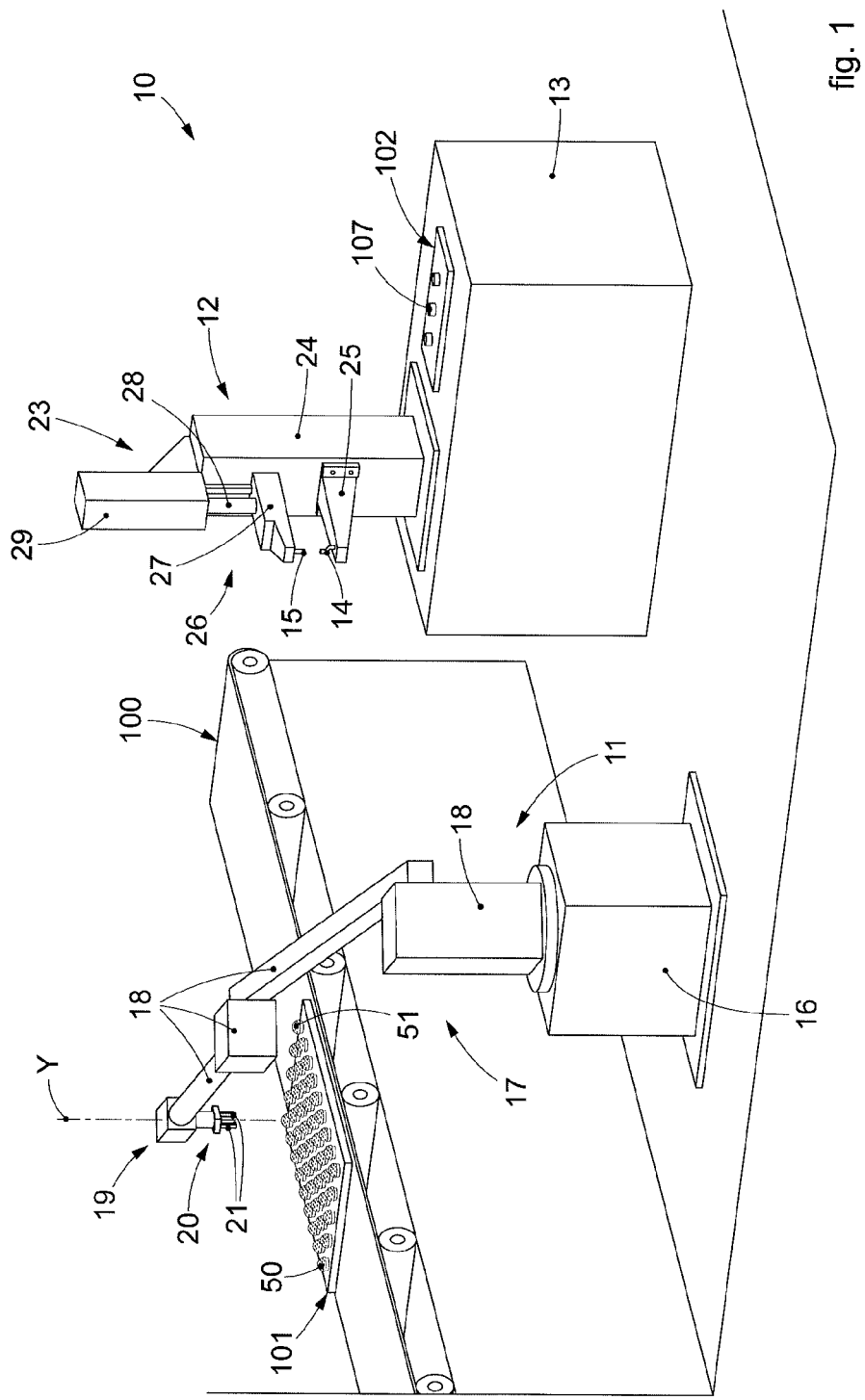
FIG. 1 is a schematic perspective view of an automated punching station according to embodiments disclosed herein.

To facilitate understanding, identical reference numbers have been used, where possible, to identify identical common elements in the figures. It is to be understood that elements and features of an embodiment can be conveniently combined or incorporated into other embodiments without further clarification.

DETAILED DESCRIPTION

Reference will now be made in detail to the possible embodiments of the invention, one or more examples of which are shown in the attached figures by way of non-limiting example. The phraseology and terminology used herein is also for non-limiting exemplary purposes.

Embodiments disclosed using the attached figures refer to an automated punching station 10 for the production of punched components 51 able, once finished, to be used in prosthetic surgery instruments.

The automated station 10 may be suitable for insertion into a robotic working line for the automated production of the aforementioned prosthetic surgery instruments.

The aforementioned punched components 51, once finished, can be used, by way of example, to produce cutting bodies such as acetabular cutters 52, patellar cutters, glenoid cutters, rasps 53, broaches 54 (FIGS. 7a-d) or similar or comparable instruments.

The punched component 51 (FIG. 3b) is obtained starting from a hollow intermediate component 50 (FIG. 3a) which has at least one external surface 60 and an opposite internal surface 70.

According to embodiments, said intermediate component 50 is obtained from a hollow untreated component on which cutting workings for the production of through holes 61, each defined by a respective edge 62 and having at least one segment BB of the edge 62 sharp, and any grinding workings for the elimination of residual elements, or burrs, that may have formed during the previous workings have been carried out.

Untreated component means an unfinished component obtained by a drawing, bending or similar operation to obtain an internal cavity identified by said internal surface 70. For example, the untreated component can be drawn starting from a flat metal sheet and, as a result, have a concave shape, more or less complex.

For example, the residual elements, or burrs, may comprise molten material formed during laser cutting of the holes. The solidified material, harder than the non-molten material, can damage or otherwise reduce the service life of punches 14 included in the punching station 10, and should preferably be removed. As a further example, the residual elements may comprise trimmings formed during a turning operation.

Each hole 61 (FIGS. 4a-b) can be peripherally defined by an edge 62, which comprises a segment BB and a complementary segment AA.

The segment AA may have a surface inclined by a cutting angle $\alpha 1$, with respect to a reference plane P tangent to the external surface 60 passing through the centre C of the hole 61 (FIG. 4a). The segment BB may have a surface inclined by a cutting angle $\alpha 2$, with respect to said reference plane P.

According to embodiments, the angle $\alpha 2$ is different from the angle $\alpha 1$, in particular is smaller, so as to make the edge BB sharp. This edge BB, or cutting edge, after a punching operation that will make it protruding (FIG. 4b), will be able to carry out a mechanical excavation on the bone. In a preferred form, the hole 61 may only be sharpened in the segment BB. Alternatively, it may be sharpened both on the segment BB and on the segment AA.

The segment BB may have an internal perimeter B1, lying on the external surface 60, and an external perimeter B2, lying on the internal surface 70.

The intermediate component 50 may comprise both the through holes 61, able to define a cutting part 55 of said cutting body 52, 53, 54 and optional auxiliary apertures functional for workings only. The auxiliary apertures may be centring notches 63, perimeter slits 64 which define a pre-cut circumference, gripping holes 65 or the like, and may be comprised in correspondence with an auxiliary band 66 (FIG. 3a).

The punching station 10 comprises at least one automated operator 11, a press device 12, and a control unit 13 (FIGS. 1, 2). The punching station 10 further comprises a transport support 100, 101 able to receive and position a plurality of intermediate components 50.

The at least one automated operator 11 is configured to pick up and move, one at a time, the intermediate components 50 from the transport support 100, 101, and to place them in cooperation with the press device 12.

The press device 12 is able to cooperate with the automated operator 11 to carry out a punching operation, on each occasion, on the segment BB of the edge 62 of the hole 61 of the intermediate component 50, for the production of a cutting part 55 of the prosthetic surgery instrument.

According to the invention, the press device 12 comprises at least one aforementioned punch 14 and a counter-punch 15, the punch 14 being fixed and the counter-punch 15 being able to move toward the punch 14 during the punching working.

The control unit 13 is configured at least to command the automated operator 11 to place in cooperation, one at a time, the intermediate components 50 with the press device 12, and to maintain each intermediate component 50 in a grip once placed in cooperation with the press device 12, and to move in a coordinated manner the automated operator 11 and the press device 12.

Within the present disclosure, the term "to place in cooperation" means that the automated operator 11 is able at least to rest the intermediate component 50 on the punch 14 in correspondence with the segment BB of the edge 62, and to accompany the intermediate component 50 in the movement direction of the counter-punch 15, or punching direction P, when the counter-punch 15 engages the intermediate component 50.

By the term "in a coordinated manner" it is meant at least that, during the punching operation, the automated operator 11 moves synchronously and in the same punching direction P with the counter-punch 15, toward the punch 14. The punching operation is intended as the working part in which the counter-punch 15 engages, or contacts, the intermediate component 50 disposed on the punch 14 and moves toward the punch 14 to produce a protruding part of the edge 62 of the hole 61 with respect to the external surface 60, from the moment in which the counter-punch 15 engages the intermediate component 50 until the instant in which the counter-punch ends its movement toward the punch 14.

Within the present disclosure, the term "synchronous" means that the aforementioned automated operator 11 is able to move together with the counter-punch 15 and with the same speed thereof. According to embodiments, the synchronous movement occurs at least during the punching operation.

According to the present disclosure, therefore, the control unit 13 is configured to move said automated operator 11 synchronously, and in the same punching direction P, with respect to said counter-punch 15, so as to accompany the intermediate component 50, maintained in a grip by the automated operator 11, in said punching direction P when said counter-punch 15 engages said intermediate component 50 in the punching operation. In fact, the automated operator 11, while maintaining in a grip the intermediate component 50, moves in a coordinated manner with the movement of the counter-punch 15, in particular when the counter-punch 15 engages the intermediate component 50 and throughout the stroke made by the mobile counter-punch 15 during punching.

Advantageously, in this way it is avoided that the intermediate component 50 undergoes an undesired deformation in the area surrounding the hole 61 during punching, thus clearly, cleanly and precisely defining the cutting part 55. Indeed, during the punching operation the internal perimeter B1 of the segment BB of the hole 61, resting on a central and protruding part of the punch 14, remains stationary, while the external perimeter B2 of the segment BB is pushed by the counter-punch 15 toward a peripheral part of the punch, not protruding (FIGS. 4a-b, 5a, 5c-d). If the intermediate component 50 were maintained fixed while the external perimeter B2 deforms under the action of the counter-punch, in the surrounding area a consequent deformation would result such as to compensate for the movement of the external perimeter B2 of the segment BB.

According to embodiments, the automated operator 11 comprises a fixed base platform 16 on which a robotic articulated arm 17 is rotatably associated.

The robotic articulated arm 17 may comprise a plurality of elements 18 rotatably articulated with respect to each other in succession, so as to allow movement of the robotic articulated arm 17 according to a number of degrees of freedom sufficient to allow the robotic articulated arm 17 to carry out all necessary manipulations and positioning.

In the present case, the robotic articulated arm 17 may be moved according to six degrees of freedom. This allows picking and/or positioning from/on the transport support 100, 101 respectively of the intermediate component 50 or the punched component 51 and subsequent manipulating operations without the intervention of an operator.

The automated operator 11, controlled by the control unit 13, can therefore allow the movement of the intermediate component 50 to obtain the desired working without the intervention of an operator.

The robotic articulated arm 17 may be provided with a manipulation head 19 for picking up and positioning the components 50, 51 in a desired manner.

According to embodiments, the robotic articulated arm may comprise, in correspondence with the manipulation head 19, a gripping device 20 for gripping the aforementioned components 50, 51.

The gripping device 20 may comprise gripping elements 21, in particular hooks 21, with reference to FIG. 1, and, by way of example, two hooks 21. In variations not shown, the gripping elements 21 can be ring-shaped bands, magnetic elements or the like.

According to embodiments and as shown in FIG. 5b, the gripping elements 21 can have coupling elements 22, able to cooperate with the gripping holes 65.

In this way it is possible for the automated operator 11 to grip the components 50, 51 firmly.

It is also possible for the automated operator 11 to grip the components 50, 51 in known positions, so as to know a priori the positioning of the holes 61 on the component 50.

The press device 12 may further comprise a device body 23.

The device body 23 may be able to support the punch 14 and the counter-punch 15.

The device body 23 may comprise a body base 24, a support element 25 for the punch 14, and a movement element 26 of the counter-punch 15.

According to embodiments, the body base 24 and the support element 25 are fixed, the movement element 26 is mobile.

As shown by way of example in FIG. 1, the movement element 26 may comprise a mobile support 27 of the counter-punch 15, and a shaft 28, able to fit into a hollow structure 29 of the body base 24.

The press device 12 can comprise actuating members, not shown in the figures, for example an electric, hydraulic motor and the like, able to move the movement element 26.

The control unit 13 comprises at least one electronic memory, and a data processing unit.

The electronic memory may be connected to the processing unit and may be one or more of those commercially available, such as random access memory (RAM), read-only memory (ROM), floppy disk, hard disk, mass memory, or any other form of digital storage, local or remote.

The electronic memory may be able to contain software instructions and data executable by the at least one processing unit to command at least the automated operator 11 and the press device 12 to carry out the punching working.

The automated station 10 can also comprise a rotation tray 102, on which the automated operator 11 can temporarily deposit the intermediate component 50, while the manipulation head 19 rotates around its own axis Y, so as to grip the component 50 in a different working position.

A plurality of modular positioning elements 107 may be present on the tray 102. Each of the modular positioning elements 107 may be associated with the tray 102 by means of appropriate positioning holes defined on the latter, not shown in the figure.

Each modular positioning element 107 is able to receive in a desired position a respective component 50. The modular positioning elements 107 may comprise adaptor elements, to support components 50 of different sizes.

The components 50, 51 may be fed to/from the automated station 10 by an operator in a manual mode.

According to embodiments not shown, the automated station 10 comprises at least one storage space able to accommodate a plurality of the aforementioned components 50, 51.

According to embodiments, the storage space comprises at least one tray 101, or transport support 101, for the components 50, 51. The tray 101 can be disposed in support, i.e. associated above, to a support structure that can comprise vertical and horizontal support elements, so as to define a shape that resembles that of the frame of a table.

On the tray 101 there can be a plurality of modular positioning elements 103, each of which is associated with the tray 101 by means of appropriate positioning holes 105 defined on the latter.

Each modular positioning element 103 is able to position in a desired manner a respective component 50, 51. The modular positioning elements 103 may include adaptor elements 104.

For example, in the case of components 50, 51 having a spherical cap shape intended for the production of acetabular cutters 52, the modular positioning elements 103 may comprise a cylindrical-shaped central body projecting from the tray 101, with which a plurality of rings 104 having a gradually decreasing diameter may be associated.

The components 50, 51 may be positioned on said modular positioning elements 103 at random or in a predefined position, for example in reference to a centring notch 63.

According to embodiments, the tray 101 may be associated with an RFID radio frequency type identification label 106, on which information relating to the components 50, 51 supported by it is stored. The aforementioned information may relate to the type, dimension or size of the components 50, 51, as well as to an identifier of completed working or similar information.

According to possible embodiments, a respective identification label 106 may be associated with each position defined on the tray 101. A respective identification label 106 may also be associated with the modular positioning elements 103 and/or the adaptor elements 104.

According to embodiments, the manipulation head 19 may comprise devices interfacing with the aforementioned identification labels 106, for reading/writing information from/on the same, for managing the punching working and any subsequent finishing workings.

In an embodiment, as shown in FIGS. 1 and 2, the punching station 10 may be connected to other stations of the robotic working line in an automatic mode, by means of a transport line 100 which comprises one or more conveying devices, for example belt, strap conveyors, or the like.

The transport line 100 can cooperate with the trays 101, for the containment of the components 50, 51. The trays 101 may have, for example on their sides, specific gripping elements in order to be manipulated and moved in an automated manner.

In an alternative embodiment not shown in the figures, the transport line 100 may be able to operate as a transport support for the components 50, 51. The transport line 100 may, in this case, comprise a plurality of modular positioning elements to which adaptor elements may possibly be associated, similarly to what is disclosed above.

In an alternative embodiment not shown, the punching station 10 may be connected to other stations of the robotic working line in a semi-automatic mode, for example by means of robotic devices for the transport of the components from one station to the next.

Embodiments disclosed herein also relate to a method to produce punched components 51 for prosthetic surgery instruments, starting from hollow intermediate components 50 provided with through holes 61 defined by a respective edge 62.

According to embodiments, the method provides to:

pick up the intermediate components 50, one at a time, from a transport support 100, 101 by means of at least one automated operator 11;

position each intermediate component 50 on a punch 14 of a press device 12 in correspondence, on each occasion, with a segment BB of the edge 62 of a hole 61 (FIG. 5*a*);

move a counter-punch 15 of the press device 12 toward the punch 14, maintaining the automated operator 11 in the above-described position until the counter-punch 15 engages the segment BB of the edge 62, as indicated by the arrow of the punching direction P (FIG. 5*c*);

continue to move the counter-punch 15 toward the punch 14 and synchronously move the automated operator 11, which maintains the intermediate component 50 in a grip, with the counter-punch 15 as indicated by the arrow of the punching direction P (FIG. 5*d*), in the same movement direction as the counter-punch 15, until the segment BB of the edge 62 assumes a protruding shape suitable for the production of a cutting part 55 of the prosthetic surgery instrument (FIG. 5*e*).

According to embodiments, the method provides to control the automated operator 11 and the press device 12 by means of a control unit 13.

The method may provide to detect the moment in which the counter-punch 15 engages the intermediate component 50 by directly or indirectly detecting parameters of the press device 12. For example, it may provide to detect the electric current required by the actuating members to move the counter-punch 15, for example by detecting the moment of engagement by means of the increase of the electric current required by the actuating member. For example, it may provide to detect by means of sensors the pressure of a fluid in the control circuits of the actuating members. According to an alternative embodiment, the method may provide to estimate the time required for the counter-punch 15 to engage the intermediate component 50, based on the distance to be travelled.

The method may provide to repeat the steps disclosed above for the other holes 61.

According to embodiments, the method may provide to divide the cutting part 55 into multiple working areas, for example into four working areas, or quadrants Q1, Q2, Q3, Q4, in case the cutting body to be obtained is an acetabular cutter 52.

The method may provide to carry out the punching working on the holes 61 of a first working area Q1. The method may then provide to rotate the intermediate component 50 around an axis X thereof to repeat the same working on the holes 61 of one or more other working areas Q3.

As an example, the intermediate component 50 may be worked initially on the working area Q1 (FIGS. 5*a, c-d*). It may then be rotated by an angle of 180° to repeat the same working on the holes 61 of the working area Q3 in case the cutting body is an acetabular cutter 52.

The method may also provide to:

carry out the punching operation on the holes 61 of one or more of the working areas Q1, Q3;

temporarily deposit the intermediate component 50 on a rotation tray 102;

rotate around its axis Y a manipulation head 19 of a robotic articulated arm 17 of the automated operator 11, for example by an angle of 90° in case the cutting body is an acetabular cutter 52;

grip the intermediate component 50 again, so that the gripping elements 21 of the manipulation head 19 leave the new one or more areas Q2, Q4 on which to carry out the working free, for example they interface only with one or more of the one or more previously worked areas, such as the previously worked quadrants Q1, Q3;

repeat the working on the holes 61 of the one or more remaining working areas, for example on the areas Q2 and Q4.

In this way, it is also possible to carry out the working on any areas temporarily covered by the gripping device 20.

According to embodiments, the method may provide, once the working has been carried out on all the holes 61, to deposit the punched component 51 on the transport support 100, 101.

In the exemplary case of an acetabular cutter 52, the method may provide to:

carry out the punching working on the first working area Q1;

rotate the intermediate component 50 around its own axis X by 180°;

carry out the punching working on the working area Q3 opposite to Q1;

deposit the intermediate component on the rotation tray 102;

rotate the manipulation head around its own axis Y by 90°;

grip the intermediate component 50, so that the gripping elements 21 of the manipulation head 19 go in cooperation with the gripping holes 65 that are located in correspondence with the working areas Q1 and Q3, leaving the working areas Q2, Q4 free;

carry out the punching working on the working area Q2;

rotate the intermediate component 50 around its own axis X by 180°;

carry out the punching working on the working area Q4 opposite to Q2.

According to one embodiment, the method therefore provides to send the punched component 51 to subsequent finishing workings, such as manual removal of the auxiliary band 66, for example along the pre-cut circumference defined by the perimeter slits 64, medical type finishing, such as polishing, washing, sterilisation or the like, and control workings to obtain a finished cutting body 52, 53, 54 (FIGS. 7a-c).

According to a preferred embodiment, the method provides that the intermediate components 50 are positioned on the transport support 100, 101, in correspondence with the modular positioning elements 103, with an orientation known to the punching station, for example in reference to a centring notch 63.

According to an alternative variant not shown in the figures, the intermediate components 50 are randomly oriented, and the orientation is recognised by a system recognising the position assumed by the intermediate component 50, such as for example a system comprising optical devices, cameras, sensors or the like, for example by means of the recognition of the position of the centring notch 63.

Advantageously, it is thus possible to know the position and orientation of the holes 61 for the punching working.

Embodiments disclosed herein relate to a punched component 51 produced by means of an automated station 10 and in accordance with the production method according to the invention, having at least a cutting part 55 delimited by an external surface 60 and an opposite internal surface 70.

According to embodiments, the cutting part 55 is provided with a plurality of through holes 61 passing from the external surface 60 to the internal surface 70, wherein each hole 61 has a segment AA and a complementary segment BB of the edge 62 that define it peripherally. The segment AA and the complementary segment BB may have different inclinations.

The segment AA may have an inclination of an angle $\alpha 1$ with respect to a reference plane P tangent to the external surface 60 passing through the centre C of the hole 61. The segment BB may have an inclination of an angle $\alpha 2$ with respect to the reference plane P. The angle $\alpha 2$ is preferably smaller than the angle $\alpha 1$.

The segment BB is able, by means of a punching operation, to assume a protruding shape suitable for the production of the cutting part 55 (FIGS. 3b, 4b, 7a-d).

It is clear that modifications and/or additions of parts or steps can be made to the automated station 10, the production method, and the punched component 51 disclosed so far, without departing from the scope of the present invention as defined by the claims.

In the following claims, the references in parentheses have the sole purpose of facilitating reading and must not be considered as limiting factors as regards the scope of protection underlying the specific claims.

The invention claimed is:

1. An automated punching station configured to produce punched components for prosthetic surgery instruments, wherein said station comprises:

a transport support arranged to receive and position a plurality of intermediate components, each of the intermediate components provided with through holes defined at least in part by a respective edge;

a press device comprising at least one fixed punch and a counter-punch mobile in a punching direction with respect to said fixed punch for punching each of said edges to provide a cutting part of the prosthetic surgery instrument;

at least one automated operator configured to pick up, and move one at a time, said intermediate components from said transport support, so as to place each intermediate component in cooperation on each occasion with said press device in order to punch the respective edge in a punching operation; and a control unit configured to command the automated operator to maintain each intermediate component in a grip once placed in cooperation with the press device and move said automated operator synchronously; and wherein, the counter-punch is configured to engage and shape a segment of the respective edge into a protruding cutting edge.

2. The automated punching station as in claim 1, wherein said automated operator is configured to rest the intermediate component on the fixed punch in correspondence with the protruding cutting edge.

3. The automated punching station as in claim 1, wherein said automated operator comprises a robotic articulated arm provided with a plurality of elements rotatably articulated with respect to each other in succession, in order to perform a movement with six degrees of freedom.

4. The automated punching station as in claim 3, wherein said robotic articulated arm is provided with a manipulation head able to pick up and position the components in a desired manner by means of a gripping device which has coupling elements with holes for gripping said components.

5. The automated punching station as in claim 1, wherein the intermediate components define a tangential reference plane, and wherein an internal perimeter of the protruding cutting edge protrudes beyond the tangential reference plane.

6. The automated punching station of claim 5, wherein each of the through holes includes a second segment, and wherein the first segment has a first cutting angle relative to the reference plane and the second segment has a second cutting angle relative to the reference plane, wherein the second cutting angle is less than the first cutting angle, and further wherein the protruding cutting edge is formed adjacent the internal perimeter of the segment of the respective edge.

7. A robotic working line in combination with the automated punching station as in claim 1, and wherein said automated punching station is arranged in the robotic working line.

8. An automated punching station configured to produce punched components for prosthetic surgery instruments, wherein said station comprises:
   a transport support arranged to receive and position a plurality of intermediate components, each of the intermediate components provided with through holes, each of the through holes having an edge;
   a press device comprising at least one fixed punch and a counter-punch movable in a punching direction with respect to the fixed punch for punching the edge of each of the through holes providing a cutting part of the prosthetic surgery instrument;
   at least one automated operator configured to pick up, and move one at a time, said intermediate components from said transport support, so as to place each intermediate component in cooperation on each occasion with said press device in order to punch the respective edge in a punching operation; and
   a control unit configured to command the automated operator to maintain each intermediate component in a grip once placed in cooperation with the press device and move said automated operator synchronously;
   wherein each of the through holes includes a first segment; and
   further wherein the counter-punch is configured to engage and shape the first segment of the respective edge, into a protruding cutting edge.

9. The automated punching station of claim 8, wherein each of the through holes includes a second segment, and wherein the first segment has a first cutting angle relative to a reference plane and the second segment has a second cutting angle relative to the reference plane, and wherein the second cutting angle is less than the first cutting angle.

10. A robotic working line for the production of prosthetic surgery instruments, comprising:
    an automated punching station arranged in the robotic working line;
    wherein the automated punching station comprises:
      a transport support arranged to receive and position a plurality of intermediate components, each of the intermediate components provided with through holes defined at least in part by a respective edge;
      a press device comprising at least one fixed punch and a counter-punch mobile in a punching direction with respect to said fixed punch for punching each of said edges to produce a cutting part of the prosthetic surgery instrument;
      at least one automated operator configured to pick up, and move one at a time, said intermediate components from said transport support, so as to place each intermediate component in cooperation on each occasion with said press device in order to punch the respective edge in a punching operation; and
      a control unit configured to command the automated operator to maintain each intermediate component in a grip once placed in cooperation with the press device and move said automated operator synchronously; and
    wherein the counter-punch configured to engage and shape a segment of the respective edge, into a protruding cutting edge.

\* \* \* \* \*